US00PP14069P39

(12) United States Plant Patent
Meilland

(10) Patent No.: US PP14,069 P3
(45) Date of Patent: Aug. 19, 2003

(54) MINIATURE ROSE PLANT NAMED 'MEIJELIOR'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 152 days.

(21) Appl. No.: 09/788,410

(22) Filed: Feb. 21, 2001

(65) Prior Publication Data

US 2003/0014783 P1 Jan. 16, 2003

(51) Int. Cl.[7] ..... A01H 5/00
(52) U.S. Cl. ..... Plt./116

(58) Field of Search ..... Plt./116, 119, 121, Plt./123, 126, 128

*Primary Examiner*—Howard J. Locker
(74) *Attorney, Agent, or Firm*—Burns, Doane, Swecker & Mathis, LLP

(57) ABSTRACT

A new and distinct variety of rose plant of the dwarf Miniature Class is provided which abundantly forms attractive double blossoms that are a blend of pale orange on the upper surface and pale pink on the undersurface. The growth habit is bushy, low and compact. Very dense medium green semi-glossy foliage is formed that contrasts nicely with the blossom coloration. The new variety is well suited for pot forcing under greenhouse growing conditions to form a distinctive gift plant. There is no particular sensitivity to diseases.

1 Drawing Sheet

Figures 1, 2, 3, 4, 5, 6, 7, 8, 9, 10, 11, 12, 13, 14, 15, 16:
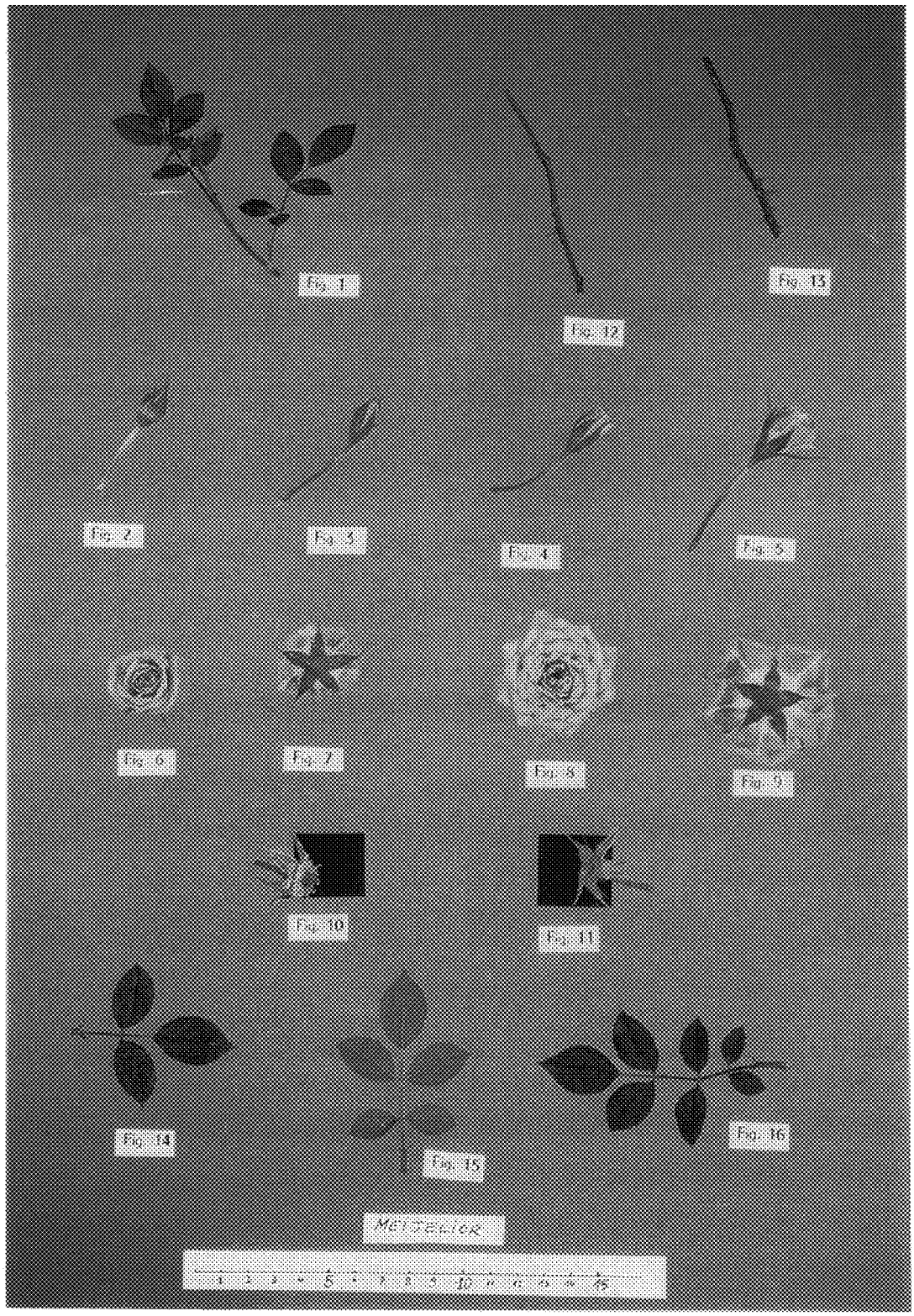

Botanical/commercial classification: Rosa hybrida / Miniature Rose Plant.
Varietal denomination: cv. 'Meijelior'.

SUMMARY OF THE INVENTION

The new variety of Rosa hybrida Miniature rose plant was created by artificial pollination wherein two parents were crossed which previously had been studied in the hope that they would contribute the desired characteristics. The female parent (i.e., the seed parent) of the new variety was the 'Meifruije' variety (U.S. Plant Pat. No. 9,033). The male parent (i.e., the pollen parent) was the product of the cross of the 'Meineyta' variety (non-patented in the United States) and the 'Meisancho' variety (non-patented in the United States). The parentage of the new variety can be summarized as follows:

'Meifruije'×('Meineyta'×'Meisancho').

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) exhibits a bushy, low and compact growth habit, (b) forms in abundance attractive very double blossoms that are pale orange on the upper surface and pale pink on the under surface, (c) forms very dense medium green semi-glossy foliage, and (d) is well suited for pot forcing under greenhouse growing conditions.

The new variety well meets the needs of the horticultural industry. It is particularly well suited for pot forcing under greenhouse growing conditions to form a distinctive gift plant.

The new variety can be readily distinguished from its parental varieties. For instance, the 'Meifruije' variety forms dissimilar bright orange flowers having a yellow edge and approximately 25 to 40 petals. The flowers of the 'Meineyta' variety display a distinctive orange blend coloration. The 'Meisancho' variety is a Floribunda rose plant and displays dissimilar geranium red flowers.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety has been named the 'Meijelior' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during May while growing on their own roots in greenhouses at LeCannet des Maures, Var, France. Dimensions in centimeters are shown at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of six month-old specimens of the new variety which were observed during November while growing on their own roots in greenhouses at LeCannet des Maures, Var, France.

Botanical classification: Rosa hybrida.
Market: Dwarf Miniature.
Plant:
*Height.*—Approximately 25 to 30 cm on average at the end of the growing season.
*Habit.*—Bushy.
Branches:
*Color.*—Young stems: near Green Group 137D. Adult wood: near Green Group 137B.
*Thorns.*—Size: medium. Quantity: moderately numerous (as illustrated). Color: on young stems pinkish, near Greyed-Red Group 181B, and on adult wood tan, near Greyed-Yellow Group 161A. Configuration: rather elongated downwards on the upper surface and hooked on the under surface.
Leaves:
*Petioles.*—Upper surface: non-glandular, and medium green, near Yellow-Green Group 147B, in coloration. Under surface: medium green, near Yellow-Green Group 147B in coloration.
*Stipules.*—Adnate, pectinate, and rather broad.
*Leaflets.*—Number: 3, 5 (most often), and 7. Shape: generally lanceolate with a symmetrical tip and an obtuse base (as illustrated). Texture: normal. Serration: regular. General appearance: very dense, medium green and semi-glossy. Size: approximately 3 cm in length on average and approximately 1.5 cm in width on average. Color (young foliage): upper surface: near Green Group 137A. under surface: near Green Group 138B. color (adult foliage): upper surface: Green Group 139A. under surface: Green Group 138A.
Inflorescence:
*Number of flowers.*—Commonly approximately 2 to 5 per stem.
*Peduncle.*—Near Yellow-Green Group 147B in coloration, medium in size, and the length commonly is approximately 2.5 to 3 cm on average.
*Sepals.*—Upper surface: tomentose and near Green Group 138B in coloration. Under surface: near Yellow-Green Group 144A in coloration. Shape: with some thin weak extensions (as illustrated).
*Buds.*—Shape: conical and pointed. Size: medium for class, and approximately 1 to 1.5 cm in length.
*Flower.*—Form: very double and cup-shaped. Diameter: approximately 5 cm on average when fully open. Color (when opening begins): upper surface: near Orange Group 29C. under surface: near Orange Group 29D suffused with Red Group 39B. Color (when blooming): upper surface: near Orange-Red Group 31C. under surface: near Red Group 37B suffused with Red Group 48B. Color (at end of opening): upper surface: near Orange Group 29D. under surface: near Orange Group 29D suffused with Red Group 39B. Fragrance: none. Anthers: near Yellow-Orange Group 17B in coloration. Pollen: moderate quantity and near Yellow Group 13B in coloration. Stamen number: approximately 125 on average. Filaments: near Yellow-Orange Group 14A in coloration. Pistil number: approximately 105 on average. Petal configuration: wedge-shaped base and reflexed edges. Petal number: approximately 64 on average. Petal drop: good, the petals detach cleanly. Stigmas: near Yellow-Orange Group 19C in coloration. Styles: near Red-Purple Group 60D in coloration. Receptacle: near Yellow-Green Group 144A in coloration. Lasting quality: very long on the plant with the blossoms commonly lasting approximately 10 to 12 days.
Development:
*Vegetation.*—Strong.
*Blooming.*—Very abundant.
*Resistance to diseases.*—Good with respect to Powdery Mildew and Botrytis.
*Aptitude to bear fruit.*—None.

I claim:

1. A new and distinct variety of Miniature rose plant characterized by the following combination of characteristics:

(a) exhibits a bushy, low and compact growth habit, (b) forms in abundance attractive very double blossoms that are pale orange on the upper surface and pale pink on the under surface, (c) forms very dense medium green semi-glossy foliage, and (d) is well suited for pot forcing under greenhouse growing conditions;

substantially as herein shown and described.

* * * * *

METERSTICK